United States Patent [19]

Briody et al.

[11] Patent Number: 4,622,431
[45] Date of Patent: Nov. 11, 1986

[54] METHOD FOR CONVERTING ORGANIC CHLOROFORMATE TO THE CORRESPONDING ORGANIC CHLORIDE

[75] Inventors: Robert G. Briody, Clinton; Henry C. Stevens, Akron, both of Ohio

[73] Assignee: PPG Industries, Inc., Pittsburgh, Pa.

[21] Appl. No.: 720,200

[22] Filed: Apr. 4, 1985

[51] Int. Cl.⁴ .................. C07C 41/18; C07C 17/33
[52] U.S. Cl. .................... 568/606; 568/610; 568/614; 568/655; 568/669; 568/681; 570/101; 570/191; 570/201
[58] Field of Search ............ 568/606, 610, 614, 655, 568/669, 681; 570/101, 191, 201

[56] References Cited

U.S. PATENT DOCUMENTS

| | | | |
|---|---|---|---|
| 2,115,192 | 4/1938 | Bruson | 260/150 |
| 3,061,552 | 10/1962 | Schenck et al. | 252/135 |
| 3,294,847 | 12/1966 | Albright et al. | 260/615 |
| 3,426,077 | 2/1969 | Eiseman et al. | 260/615 |
| 3,437,697 | 4/1969 | Hodgkiss et al. | 260/615 |

OTHER PUBLICATIONS

Dimethylformamide-Catalyzed Decarboxylation of Alkyl Chloroformates, Reinhard Richter et al, J. Org. Chem., 1983, 48, 2625–2627.
The Chemistry of Chloroformates, M. Matzner et al., Chem. Rev. 64, pp. 645–661 and 677–687 (1964).
Richter et al, Jour. Org. Chem 48(1983) 2625–2627.

*Primary Examiner*—Bernard Helfin
*Attorney, Agent, or Firm*—Irwin M. Stein

[57] ABSTRACT

Organic chloroformate compounds are decomposed to their corresponding chlorides by heating the chloroformate, e.g., between 100° and 175° C., in the presence of a catalytic amount of solid poly(vinylpyridine), e.g., poly(4-vinylpyridine), for a time sufficient to convert the chloroformate to the corresponding chloride.

19 Claims, No Drawings

METHOD FOR CONVERTING ORGANIC CHLOROFORMATE TO THE CORRESPONDING ORGANIC CHLORIDE

DESCRIPTION OF THE INVENTION

A variety of organic sulfonate compounds are used commercially as surfactants. One method described for producing sulfonate-type surfactants involves the reaction of the chlorine capped precursor compound with sodium sulfite. See, for example, U.S. Pat. No. 2,115,192. The chlorine capped precursor compound has been prepared by chlorinating the corresponding alcohol with phosphorus trichloride or thionyl chloride. When phosphorus trichloride is used as the chlorinating agent, difficulties in separating by-products, such as phosphorous acid, from the resulting principal chloride product are experienced. Thionyl chloride is economically unattractive as a chlorinating agent because of its cost and because it is a highly corrosive material. Moreover, it produces sulfur dioxide as a by-product of the chlorination reaction.

It has now been found that conversion of organic alcohols, e.g., the alcohol precursors of sulfonate surfactants, to the corresponding chloroformate and subsequent decomposition of such chloroformate to the corresponding chloride compound can be achieved readily and economically. In the process described hereinafter, the organic alcohol is reacted with phosgene and the resulting chloroformate converted to the corresponding chloride by heating the chloroformate in the presence of a catalytic amount of a solid poly(vinylpyridine) catalyst for a time sufficient to achieve the foregoing conversion. In particular, the corresponding chlorides derived from organic chloroformate compounds, especially organic chloroformate compounds useful as intermediates in the preparation of anionic surfactant materials, are obtained by heating the chloroformate at between about 100° C. and 175° C. in the presence of a catalytic amount of a solid poly(4-vinylpyridine) catalyst for between about 0.5 and 10 hours. Use of the solid poly(vinylpyridine) catalyst permits preparation of a more pure chlorine capped precursor compound since the solid catalyst and liquid reaction product are readily separated by any convenient liquid-solid separation technique, e.g., filtration. By-product carbon dioxide generated during decomposition of the chloroformate is also readily removed from the reaction medium and liquid reaction product as a gas.

DETAILED DESCRIPTION

Poly(vinylpyridine) that may be used as the catalyst in the present process may be derived from 2-, 3- or 4-vinylpyridine and copolymers of such vinyl pyridines, e.g., copolymers of vinyl pyridine with styrene, containing at least 75 weight percent of the vinyl pyridine. From about 1 to 3 weight percent of a cross-linking agent, such as divinyl benzene, may also be used to prepare the aforesaid polymers and copolymers. Cross-linked poly(4-vinylpyridine) is readily available commercially from Reilly Tar & Chemical Corporation. The catalyst is a finely-divided, cross-linked, usually granular polymer that is insoluble in common organic solvents such as methanol, acetone, toluene, hexane, ethyl acetate, and isopropanol. The catalyst should be stable to temperatures of at least 175° C. As used herein, the term poly(vinylpyridine) is meant to include polymers and copolymers of vinyl pyridines.

Because the poly(vinylpyridine) is a solid material, it can be recycled and reused several times without further treatment to process further chloroformate compound to its corresponding chloride. When the activity of the catalyst diminishes from continued use, its catalytic activity may be regenerated by treating it with an aqueous basic reagent, e.g., sodium hydroxide, and drying the catalyst in air.

The poly(vinylpyridine) catalyst will typically contain adsorbed moisture. Although such a "wet" catalyst can be used in the present process, it is preferred that the catalyst be dried before use so as to avoid the formation of hydrogen chloride vapors and organic carbonate impurities during decomposition of the chloroformate. Drying of the catalyst so that it is substantially free of water can be readily accomplished by heating it in a vacuum oven at from 90°–110° C. until constant weight is achieved.

Solid, finely-divided, e.g., granular, poly(vinylpyridine) is used in the present process in catalytic amounts, i.e., an amount sufficient to catalyze the decomposition of the organic chloroformate compound to the corresponding organic chloride compound. Typically, between about 1 and about 20 weight percent, e.g., 10 weight percent, of the solid catalyst is used, basis the organic chloroformate compound.

In accordance with the process of the present invention, the organic chloroformate compound is brought into contact with the poly(vinylpyridine) solid catalyst and heated for a time sufficient to convert substantially all of the chloroformate compound to the corresponding chloride. The temperatures at which the aforesaid conversion occurs will vary depending on the organic chloroformate compound; but, will typically be in the range of between about 100° C. and about 175° C., e.g., between about 130° C. and 155° C. The conversion may be accomplished at ambient pressures, although superatmospheric and subatmospheric pressures may be utilized. Heating of the chloroformate compound is carried out for a time sufficient to convert substantially all, e.g., at least 95, preferably at least 98, weight percent of the chloroformate to the chloride. The times required to accomplish such substantial conversion will vary and depend on the chloroformate compound employed and the amount and activity of the catalyst. Commonly, substantial conversion to the chloride is accomplished in between about 0.5 and about 10 hours, more particularly between 1 and 6 hours.

The organic chloride reaction product can be separated from the solid poly(vinyl pyridine) catalyst by any convenient solid-liquid separating means, e.g., filtration, decantation, centrifugation, etc. Filtration is a relatively inexpensive expedient means to accomplish the aforesaid separation.

In a preferred embodiment, the liquid organic chloride reaction product is purified by contact with a suitable solid adsorbant, e.g., activated carbon, alumina, and silica to remove contaminating traces of colored impurities that may have been imparted to the reaction product from the catalyst.

The process of the present invention is applicable to organic haloformate compounds, particularly organic chloroformate and bromoformate compounds, i.e., compounds of the graphic formula, $R\text{-}(OR')_xOC(O)X$, wherein X is halogen, e.g., chlorine and bromine. The present process is particularly and advantageously utilized for the conversion of organic chloroformate compounds that are used as precursors of organic sulfonates (and salts thereof, e.g., the sodium, potassium, lithium, calcium and ammonium salts) that have found application as surfactants and in related fields of application. Exemplary of the organic haloformate compounds to which the process of the present invention can be applied are organic chloroformates of the graphic formula, R—(OR')$_x$OC(O)Cl  I In the above formula I, R is selected from the group consisting of C$_1$–C$_{30}$ linear and branched alkyl, C$_5$–C$_6$ cycloalkyl, C$_1$–C$_4$ alkyl-substituted C$_5$–C$_6$ cycloalkyl, phenyl, alkyl substituted phenyl of the graphic formula, (R")$_a$Ph—, wherein Ph is phenylene, R" is C$_1$–C$_{18}$ alkyl and a is an integer of from 1 to 3, phen(C$_1$–C$_{18}$)alkyl, and C$_1$–C$_{18}$ alkyl-substituted phen(C$_1$–C$_{18}$)alkyl having a total of from 8 to about 28 carbon atoms, R' is the substituted ethylene group, —CH$_2$—CH(R''')—, wherein R''' is selected from hydrogen, methyl, ethyl and mixtures thereof, and x is a number from 0 to 40. When R in formula I is phenyl or alkyl substituted phenyl, x is at least 1. Treatment of the foregoing organic haloformate, e.g., chloroformate, compounds in accordance with the process of the present invention results in the preparation of the corresponding halide, e.g., chloride, compound, e.g., compounds of the graphic formula, R—(OR')$_x$Cl  II The organic chloride compounds of formula II can be readily converted to the corresponding sulfonates by reaction of the chloride with an alkali metal sulfite, e.g., sodium, potassium, lithium, or ammonium sulfite, as disclosed in U.S. Pat. No. 2,115,192. The sulfonation reaction is typically conducted at between 150° C. and 170° C. and pressures of between about 60 (413.7 kPa) and 115 psi (792.9 kPa) for about 16 to 20 hours. See, for example, U.S. Pat. No. 4,329,268.

In the above formula I, R may be a C$_1$–C$_{30}$ branched or straight chain alkyl. This alkyl group is typically derived from primary and secondary alcohols. R may be derived from a single alcohol or a mixture of alcohols that are derived from natural fats and oils or petroleum fractions. The particular alkyl group used will depend on the ultimate application to which the sulfonate end product is intended. For example, the number of carbon atoms for the R alkyl group may range from 1 to 30 carbon atoms, particularly 8 to 18 carbon atoms, e.g., from 11 to 15 carbon atoms. The mix of alkyl groups can vary and depends frequently on the particular manufacturer of the alcohol compounds from which the alkyl group is derived.

The alkyl substituents of the alkyl substituted phenyl radicals will typically be a branched or straight chain hydrocarbon containing from 1 to 18 carbon atoms. The phenyl radical may contain from 1 to 3 of such alkyl substituents, more commonly 1 or 2 of such alkyl substituents. Similarly the aralkyl and alkaralkyl radicals will have from 1 to 18 carbon atoms in the alkyl portion(s) of the aforesaid radicals. With respect to the alkyl substituted phenalkyl radicals, the total number of carbon atoms in such radicals will commonly range from about 7 to 28 carbon atoms.

Alcohol precursor compounds containing polyoxyalkylene groups which fall within the scope of formula I are produced by reacting the corresponding alcohol with an alkylene oxide in the presence of a catalyst. The alkylene oxide can contain, for example, from 2 to 4 carbon atoms and is the precursor of the substituted ethylene group, —CH$_2$—CH(R''')—. More particularly, the alkylene oxide may be ethylene oxide, propylene oxide, or 1,2-butylene oxide. Also contemplated are compounds containing mixtures of alkylene groups, e.g., mixtures of ethylene oxide and propylene oxide, and propylene oxide and butylene oxide. The number of alkyleneoxy groups present in the compound can vary from 1 to about 40. The designation in formula I of the number of alkylene oxide units present per mole of the aforedescribed organic molecule, i.e., the letter "x", designates the average number of moles of alkylene oxide present per mole of organic molecule, e.g., ethoxylated alcohol chloroformate, chloride or sulfonate, and hence the value of x in graphic formula I may be a fractional number between 1 and 40. Even though "x" is denoted as an integer number of alkylene oxide units, each organic molecule contains a distribution of units with the "x" value representing the average number of moles of alkylene oxide per mole of organic molecule. When x is 0 in formula I, the chloroformate compound contains no poly(alkylene oxide) groups, which would be representative of alkyl chloroformate, arylchloroformate, linear or branched alkylbenzylchloroformate, etc. compounds.

Organic chloroformate compounds represented by graphic formula I may be used as precursors of derivative sulfonate compounds, many of which are used as surfactants. Examples of such sulfonate materials are the alkane and aralkyl sulfonates, the sulfonated polyoxyalkylene alkyl phenols and ethoxylated and sulfonated alcohols generally. These materials can be prepared by techniques known in the art. In accordance with the present process, the corresponding alcohol is reacted with phosgene to prepare the corresponding chloroformate, which is decomposed to the corresponding chloride, and this chloride compound reacted with sodium sulfite to form the corresponding sulfonate compound.

In accordance with a preferred embodiment of the present invention, liquid organic chloroformate compound is introduced into a nitrogen purged reaction vessel containing stirring means. About 10 weight percent of granular poly(4-vinylpyridine) catalyst is also charged to the reaction vessel and the contents heated to between about 130° and 155° C. for about 3 to 5 hours. During the heating period, carbon dioxide is removed from the reaction vessel and forwarded to a scrubber and vent system to remove contaminants, e.g., hydrogen chloride and phosgene, which may not be discharged to the atmosphere. Accordingly, the scrubber system should contain chemical means for scrubbing out acidic materials. Carbon dioxide removed from the reaction vessel may be scrubbed from the vent gas by reaction with a suitable hydroxy compound, e.g., lime or barium hydroxide, to produce the corresponding alkaline earth metal carbonate. The resulting liquid organic chloride reaction product is separated from the granular catalyst by filtration and then passed over a packed bed of alumina to remove any color imparted to the chloride from traces of colored impurities present in the catalyst.

The process of the present invention is more particularly described in the following examples which are intended as illustrative only since numerous modifications and variations therein will be apparent to those skilled in the art.

EXAMPLE I

A 200 milliliter flask equipped with a magnetic stirring bar was flushed with nitrogen to dry the flask and then charged with 5 grams of granular poly(4-vinylpyridine) catalyst. The catalyst had a bulk density of about 0.45 grams per milliliter, a skeletal density of 1.154 grams per cubic centimeter, an apparent pKa of 5.8 and a hydrogen ion capacity of 8.5 meq/gram (basis dried catalyst in toluene). 54.3 grams of the chloroformate of ethoxylated lauryl alcohol having an average of 4 ethylene oxide groups, i.e., $[C_{12}H_{25}(OC_2H_4)_4OC(O)Cl]$, was then added to the reaction flask and the nitrogen purged stopped. The reaction flask was connected to a scrubber containing a sodium hydroxide-barium chloride aqueous solution. The scrubbing solution was prepared by slurrying about 20 grams of sodium hydroxide, about 15 grams of barium chloride and about 200 grams of water and filtering the resulting mixture.

The contents of the reaction flask were heated with agitation to about 100° C., at which temperature the color of the reaction mixture became green. Bubbling of the reaction mixture occured at about 135°–140° C. and a fine precipitate was observed to form in the scrubber solution. The temperature of the reaction mixture was maintained at between about 140° C. and about 150° C. for about 5 hours, at the end of which time bubbling in the reaction mixture appeared to have stopped. The total reaction time at temperatures greater than 100° C. was 6 hours. The reaction mixture was filtered to separate the granular catalyst therefrom. The resulting filtrate was an orange-brown liquid. A sample of the reaction mixture was analyzed by infrared and chemical analysis. Such analyses indicated that the chloroformate functional group was completely gone. Chlorine analysis of the reaction product by potentiometric titration after combustion in a Parr peroxide bomb was 8.67 percent (93.2 percent of theoretical).

EXAMPLE 2

A fresh sample of granular poly(4-vinylpyridine) was dried in a vacuum oven at between 90° C. and 100° C. for 5 hours. The dried poly(4-vinylpyridine) (5.0 grams) was charged to a 200 milliliter reaction flask which was flushed with nitrogen. About 50 grams of the chloroformate of an ethoxylated mixture of alcohols containing from 12 to 15 carbon atoms, and an average of 4-ethylene oxide groups, i.e., $[C_{12-15}(OC_2H_4)_4OC(O)Cl]$, was then charged to the reaction flask. The reaction mixture was heated to about 150° C. with stirring. Bubbling of the reaction mixture occurred at a reasonable rate between 140° and 150° C. Bubbling of the reaction mixture appeared to stop between 2½ to 3 hours at temperatures of about 150° C. The reaction mixture was cooled after three hours at 150° C. The reaction mixture was filtered and chlorine analysis by potentiometric titration after combustion in a Parr bomb of a sample of the filtrate found 8.64 percent chlorine (97 percent of theoretical).

EXAMPLE 3

The procedure of Example 2 was followed except that 83.6 grams of dried poly(4-vinylpyridine) catalyst and 796.2 grams of the chloroformate were added to a 2 liter reaction flask. The resulting slurry was stirred and heated to about 100° C., at which temperature a few bubbles were observed on the surface of the reaction mixture. Heating of the reaction mixture continued until the temperature reached about 130° C. whereat a significant evolution of gas was observed. The reaction temperature continued to rise to about 143° C. The temperature of the reaction mixture was maintained at about 140° C. for an additional 107 minutes. Total time at temperature of 100° C. or higher was 131 minutes. The reaction mixture was filtered and decolorized with carbon. Analysis of the filtrate showed a chlorine analysis of 8.76 percent (98.5 percent of theoretical).

While the process of the present invention has been exemplified by the use of chloroformates of ethoxylated alcohols, it is expected that similar results will be obtained using chloroformates of non-ethoxylated alcohols, such as those chloroformates coming within the scope of graphic formula I wherein x in Formula I is zero, since conversion of the chloroformate function to the corresponding chloride should not be affected by that portion of the chloroformate compound derived from the alcohol.

While the invention has been described in detail with respect to certain embodiments thereof, it is to be understood that the invention is not intended to be limited to such details except as and insofar as they appear in the appended claims.

We claim:

1. A method for preparing the corresponding chloride of an organic chloroformate of the graphic formula,

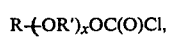

wherein R is selected from the group consisting of $C_1$–$C_{30}$ alkyl, $C_5$–$C_6$ cycloalkyl, $C_1$–$C_4$ alkyl-substituted $C_5$–$C_6$ cycloalkyl, phenyl, alkyl substituted phenyl of the graphic formula, $(R'')_a Ph—$, wherein Ph is phenylene, $R''$ is $C_1$–$C_{18}$ alkyl and a is an integer of from 1 to 3, phen($C_1$–$C_{18}$)alkyl, and $C_1$–$C_{18}$ alkyl-substituted phen($C_1$–$C_{18}$)alkyl having a total of from 8 to about 28 carbon atoms, $R'$ is the substituted ethylene group, $—CH_2—CH(R''')—$, wherein $R'''$ is selected from hydrogen, methyl, ethyl and mixtures thereof, and x is a number from 0 to 40, provided that when R is phenyl or alkyl substituted phenyl, x is at least 1, which comprises heating said chloroformate in the presence of a catalytic amount of solid poly(vinylpyridine) catalyst for a time sufficient to convert said chloroformate to the corresponding chloride.

2. The method of claim 1 wherein the organic chloroformate is heated to between about 100° C. and 175° C.

3. The method of claim 2 wherein the organic chloroformate is heated to between about 130° C. and 155° C.

4. The method of claim 2 wherein the organic chloroformate is heated for between about 0.5 and about 10 hours.

5. The method of claim 3 wherein the organic chloroformate is heated for between about 1 and about 6 hours.

6. The method of claim 1 wherein the poly(vinylpyridine) catalyst is a poly(4-vinylpyridine).

7. The method of claim 6 wherein the poly(vinylpyridine) catalyst is a cross-linked, granular polymer.

8. The method of claim 1 wherein the poly(vinylpyridine) catalyst is substantially free of water.

9. The method of claim 1 wherein between about 1 and about 20 weight percent of the solid catalyst, basis the organic chloroformate compound, is used.

10. The method of claim 1 comprising the further step of separating the solid catalyst from the organic chloride liquid product.

11. The method of claim 10 wherein the organic chloride liquid product is treated with a solid adsorbant to remove contaminating traces of colored impurities.

12. The method of claim 1 wherein the organic chloroformate is heated at between 100° C. and 175° C. for between 0.5 and 10 hours in presence of from about 1 to about 20 weight percent, basis the chloroformate, of the catalyst.

13. The method of claim 12 wherein the catalyst is a crosslinked granular poly(4-vinylpyridine) that is substantially free of water.

14. A method for preparing the corresponding chloride derivative of an organic chloroformate of the graphic formula, $$R\text{---}(OR')_x OC(O)Cl,$$

wherein R is selected from the group consisting of $C_1$–$C_{30}$ alkyl, phenyl, alkyl substituted phenyl of the graphic formula, $(R'')_a Ph\text{---}$, wherein Ph is phenylene, $R''$ is $C_1$–$C_{18}$ alkyl and a is an integer of from 1 to 3, phen($C_1$–$C_{18}$)alkyl, and $C_1$–$C_{18}$ alkyl-substituted phen($C_1$–$C_{18}$)alkyl having a total of from 8 to about 28 carbon atoms, R' is the substituted ethylene group, $-CH_2-CH(R''')-$, wherein $R'''$ is selected from hydrogen, methyl, ethyl and mixtures thereof, and x is a number from 0 to 40, provided that when R is phenyl or alkyl substituted phenyl, x is at least 1, which comprises heating said chloroformate at between about 100° C. and 175° C. for between about 0.5 and 10 hours in the presence of between about 1 and about 20 weight percent, basis the chloroformate, of a solid poly(vinylpyridine) catalyst, thereby to convert said chloroformate to the corresponding chloride.

15. The method of claim 14 wherein the chloroformate is heated between 130° C. and 155° C. for between 1 and about 6 hours.

16. The method of claim 14 wherein the poly(vinylpyridine) catalyst is a cross-linked poly(4-vinylpyridine) catalyst.

17. The method of claim 14 wherein the poly(vinylpyridine) catalyst is substantially free of water.

18. The method of claim 16 wherein the poly(vinylpyridine) catalyst is substantially free of water.

19. A method for preparing the corresponding halide of an organic haloformate of the graphic formula, $$R\text{---}(OR')_x OC(O)X$$

wherein X is halogen, R is selected from the group consisting of $C_1$–$C_{30}$ alkyl, $C_5$–$C_6$ cycloalkyl, $C_1$–$C_4$ alkyl-substituted $C_5$–$C_6$ cycloalkyl, phenyl, alkyl substituted phenyl of the graphic formula, $(R'')_a Ph\text{---}$, wherein Ph is phenylene, $R''$ is $C_1$–$C_{18}$ alkyl and a is an integer of from 1 to 3, phen($C_1$–$C_{18}$)alkyl, and $C_1$–$C_{18}$ alkyl-substituted phen($C_1$–$C_{18}$)alkyl having a total of from 8 to about 28 carbon atoms, R' is the substituted ethylene group, $-CH_2-CH(R''')-$, wherein $R'''$ is selected from hydrogen, methyl, ethyl and mixtures thereof, and x is a number from 0 to 40, provided that when R is phenyl or alkyl substituted phenyl, x is at least 1, which comprises heating said haloformate in the presence of a catalytic amount of solid poly(vinylpyridine) catalyst for a time sufficient to convert said haloformate to the corresponding halide.

* * * * *